United States Patent [19]

Yoo et al.

[11] 4,176,085

[45] Nov. 27, 1979

[54] PALLADIUM-CONTAINING CATALYST

[75] Inventors: Jin S. Yoo, South Holland, Ill.; Ronald L. Milam, Media, Pa.

[73] Assignee: Atlantic Richfield Company, Philadelphia, Pa.

[21] Appl. No.: 585,227

[22] Filed: Jun. 9, 1975

Related U.S. Application Data

[60] Division of Ser. No. 320,164, Jan. 2, 1973, Pat. No. 3,920,763, and a continuation of Ser. No. 53,654, Jul. 9, 1970, abandoned.

[51] Int. Cl.$^2$ .............................................. B01J 31/22
[52] U.S. Cl. ............................... 252/428; 252/429 B; 252/430; 252/431 C; 252/431 P; 585/509
[58] Field of Search ................... 252/428, 430, 429 B, 252/431 C, 431 P

[56] References Cited

U.S. PATENT DOCUMENTS

| 3,398,209 | 8/1968 | Schneider | 252/429 B X |
| 3,592,869 | 7/1971 | Cannell | 252/429 B X |

OTHER PUBLICATIONS

"Hydrogenation of Aromatics With Complex Metal Catalysts", Lapporte et al, J. Org. Chem., 28, (Jul., 1963), pp. 1947–1948.

*Primary Examiner*—Patrick Garvin
*Attorney, Agent, or Firm*—John B. Goodman

[57] ABSTRACT

Solid π-allyl complex catalysts comprising:
(A) A palladium source;
(B) A monotertiary phosphine electron donor ligand;
(C) A combination of a reducing agent capable of reducing the palladium source to an oxidation state of less than 2 and a Lewis acid capable of forming a coordination bond with palladium; and
(D) An acidic, solid, silica-based support material, are useful in the codimerization of a conjugated diene and a monoene. Preferably, the catalyst is activated by the additional presence of a conjugated diene. In a preferred embodiment, the solid π-allyl palladium complex catalyst prepared from palladium acetylacetonate, triphenylphosphine, diethylaluminum chloride and a calcined silica-alumina support having a separate, distinct alumina phase is useful in the selective codimerization of 1,3-butadiene and ethylene to form trans-1,4-hexadiene.

11 Claims, No Drawings

PALLADIUM-CONTAINING CATALYST

This is a division, of application Ser. No. 320,164, U.S. Pat. 3,920,763, filed Jan. 2, 1973, and a continuation of application Ser. No. 53,654, filed July 9, 1970, now abandoned.

This invention relates to novel π-allyl complex catalyst compositions and their use in the polymerization of olefins. In particular aspects, the invention relates to solid, π-allyl-complex catalyst compositions comprising a palladium source, a combination of a reducing agent capable of reducing the palladium source to an oxidation state of less than 2 and Lewis acid capable of forming a coordination bond with palladium, a monotertiary phosphine electron donor ligand and an acidic, solid, silica-based material and the use thereof in the codimerization of conjugated dienes with monoenes to form 1,4-dienes.

Homogeneous catalysts comprising a palladium compound, an aluminumalkyl halide reducing agent and compounds of a Group V-A or VI-A element are shown in the art and have previously been utilized in the dimerization of 1,3-dienes with ethylene to form trans 1,4-dienes. U.S. Pat. No. 3,398,209 discloses that such catalysts exhibit catalytic activity in the preparation of trans 1,4-dienes. The preparation of the trans isomer in substantial yields is advantageous because the trans isomers of 1,4-dienes are useful in preparing vulcanizable terpolymers with ethylene and propylene.

Numerous disadvantages are, however, attendant the use of such homogeneous catalysts in the preparation of trans-1,4-dienes, and the use of the solid catalysts described herein is advantageous in a number of these respects. The use of the solid catalysts in a fixed bed, slurry or other form eliminates the necessity for the separation of the soluble catalytic species from the products and thus eliminates catalyst losses occurring during such separation. Also, since the catalytic species herein is firmly fixed upon the acidic, solid, silica-based material through either a coordination bond or an electrostatic ionic bond formed through an ion exchange mechanism, the catalyst is remarkably stable, even after extended exposure to the atmosphere, and the deposition of metallic palladium attendant the use of the soluble homogeneous catalyst species is thus minimized. Furthermore, since the level of catalytic activity exhibited by the solid catalysts is higher than in the homogeneous counterpart catalysts, reduced reaction or contact times may be used.

In short, the acidic, silica-based material employed in the solid catalysts is not only an effective supporting matrix for the π-allylpalladium complexes prepared in situ in the system to give an active solid catalyst, but also the support acts as a cocatalyst.

Additionally, if inactivated, the solid catalyst of this invention is easily reactivated by the addition of a fresh portion of reducing agent—Lewis acid or monotertiary phosphine electron donor ligand or a combination of these two components. This ease of reactivation is attributable at least in part to the firm fixation of the metal source to the support material and resultant catalyst stability. Also, since the solid catalyst is useful in a fixed bed, slurry or other form, economic, continuous production of trans-1,4 dienes is achieved. Another advantage of the present catalyst is the versatility thereof in both liquid phase and vapor phase reactions.

It has been found that π-allyl complex catalyst compositions of a palladium source, a monotertiary phosphine electron donor ligand and a combination of a Lewis acid capable of forming a coordination bond with palladium and a reducing agent capable of reducing the palladium source to an oxidation state of less than 2, when supported on an acidic, solid, silica-based material, provide catalysts of highly desirable physical and chemical characteristics for an improved preparation of trans 1,4-dienes from conjugated dienes and monoenes. To obtain such compositions, the catalyst forming reactants can be combined in a molar ratio of electron donor ligand to palladium of about 0.5 to 15:1, preferably about 1 or 3 to 10:1 or even about 3 to 5:1, and a Lewis acid-reducing agent to palladium molar ratio of about 2 to 40:1, preferably about 5 to 12:1. The amount of Lewis acid-reducing agent to electron donor ligand can vary in more or less direct proportion with the molar ratio of electron donor to palladium source. The molar ratio of Lewis acid-reducing agent to electron donor ligand can often be between about 0.5 to 15:1, preferably between about 1 to 10:1. The weight ratio of acidic, solid, silica-based support material to palladium source normally varies between about 2 to 2000:1, preferably about 5 to 200:1 and most advantageously between about 10 to 50:1.

In the preparation of the catalyst compositions of the present invention, the palladium is provided by compounds of the metal which are preferably at least partially soluble in some solvent wherein palladium, monotertiary phosphine electron donor ligand and Lewis acid-reducing agent combination complex or a palladium and monotertiary phosphine electron donor ligand complex can be formed. Preferred are the weak field ligand complexes, the ligands of which readily serve in solution as transfer agents. Suitable sources of the palladium can include, for example, inorganic salts and bases such as $PdCl_2$, $PdBr_2$, $PdI_2$, $PdSO_4$, $Pd(OH)_2$, $PdCl_4 \cdot 2KCl$ and $Pd(No_3)_2$; dihydrocarbyloxy palladium compounds of the formula $Pd(OR)_2$ wherein R is an alkyl, aryl, aralkyl or a like group and combinations thereof; hydrocarbyloxy palladium carboxylates of the formula (RO) Pd OOCR', wherein R and R' are as defined above for R; and phosphine complexes such as diphosphine complexes of the formula $Pd[(C_6H_5)_2 PC_2H_4P(C_6H_5)_2]X$ wherein X is a halide. Also, available as a palladium source are chelates formed by palladium and weak field ligands such as β-diketones and β-keto carboxylic acids, esters and salts thereof. Examples of these palladium sources include β-diketonato palladium (II), acetylacetonato palladium (II), propionylacetonato palladium (II), benzoylacetonato palladium (II); other chelates from β-keto carboxylic acids, esters and salts thereof; salts of saturated monocarboxylic acids, e.g. palladium formate, palladium propionate, palladium caproate, palladium octoate, palladium palmitate, palladium stearate and the like; salts of corresponding unsaturated monocarboxylic acids, e.g. palladium acrylate, palladium methacrylate, palladium oleate and the like; salts of saturated dicarboxylic acids, e.g. palladium adipate, palladium succinate, palladium decane-1,10-dicarboxylate and the like; salts of corresponding unsaturated dicarboxylic acids, e.g. palladium muconate and the like; salts of cyclic and aromatic carboxylic acids, e.g., palladium cyclohexane carboxylate, palladium benzoate, palladium phthalates; and palladium dialkoxycarboxylates, e.g. palladium dimethoxyacetate. Preferred sources of palladium are those wherein the R and R' groups contain less than about 10 carbon atoms. A particularly advantageous source of palladium is palladium acetylacetonate.

The Lewis acid and the reducing agent functions of the catalysts of this invention are preferably supplied in a single compound. As examples of such compounds there may be mentioned the acidic metal halides which correspond to the general formula:

$$R'_{(n-y)}MX_y,$$

wherein M is a metallic element of coordination number n whose halides are Lewis acids, X is a halogen having an atomic number of 9 to 53, i.e., fluorine, chlorine, bromine, iodine, R' is hydrocarbyl of up to about 20 carbon atoms, particularly alkyl groups of 2 to about 10 carbon atoms and y is a number having a value from 1 to at least one less than n so that at least one R' hydrocarbyl group is present. Preferred metallic elements in the above formula include aluminum, magnesium, beryllium, mercury, lead, zinc, and tin. A particularly advantageous metal is normally aluminum. Examples of suitable acidic metal halides include alkylaluminum halides including mono-, sesqui-, and dihalides. Specific examples of suitable alkylaluminum halides are diethylaluminum chloride, fluoride, iodide, and bromide; ethylaluminum dichloride; ethylaluminum sesquichloride, etc.

When the particular reducing agent employed in the composition does not also perform as Lewis acid, it is necessary to separately supply the Lewis acid to the catalyst composition. Examples of reducing agents which are suitable in the preparation of the catalyst composition but which do not perform as Lewis acids themselves include trialkylaluminums, monoalkoxydialkylaluminums and dialkylaluminum hydrides wherein the alkyl and alkoxy groups contain up to about 10 carbon atoms. Other examples are Grignard reagents, allyl and alkyl tin complexes, and the like. The reducing agent should be compatible with the Lewis acid and capable of reducing the palladium source, advantageously palladium acetylacetonate, to an oxidation state lower than 2, preferably even to 0.

The Lewis acid component can be supplied by a compound which is other than a protonic or hydrogen acid and which is capable of receiving one or more pairs of electrons to form a coordination bond. Lewis acids are well known to the art and are defined for example by Noller, Chemistry of Organic Compounds, W. B. Saunders, 1951, at pages 233–235, by Stone, Chemical Review (1958) at page 101, and by G. N. Lewis, Journal of the Franklin Institute (1938), pages 226–293. Examples of Lewis acids which are not included as a component of a compound which also serves as a reducing agent include boron-trifluoride, boron-trifluoride etherates, e.g. diethyletherate, aluminum trihalides, zinc halides and stannic halides.

The electron donor ligand component of the catalysts of this invention are monotertiary phosphines of the formula (R)$_3$P where R is an essentially hydrocarbyl group of 1 to about 20 carbon atoms, optionally substituted with non-deleterious groups. Preferably R is a hydrocarbon group selected from alkyl, including cycloalkyl, alkaryl, aralkyl and aryl groups of up to about 20 carbon atoms. Exemplary of such groups are ethyl, isobutyl, hexyl, decyl, octadecyl, cyclohexyl, benzyl, phenyl, tolyl, and naphthyl. Trialkyl phosphines wherein the alkyl groups contain less than about 10 carbon atoms such as tri-n-butyl phosphine and triaryl phosphines such as triphenylphosphine have been found to be particularly advantageous.

The solid supports suitable for use in the catalysts of this invention are acidic, solid, silica-based materials, e.g., having a D+L activity of at least about 20, preferably at least about 30, when determined according to the method of Birkhimer, et al., "A Bench Scale Test Method for Evaluating Cracking Catalysts," Proceedings of the American Petroleum Institute, Division of Refining, Vol. 27(III), page 90 (1947) and hereinafter referred to as Cat A. The silica-based support preferably has a substantial surface area as determined by the BET nitrogen absorption procedure (JACS, Vol. 60, pp. 309 et seq., 1938). The surface area of the support can be at least about 50 square meters per gram, and such surface areas are often up to about 500 or more m$^2$/gm, preferably about 150 to 400 m$^2$/gm. It is preferred that the catalyst support be relatively dry to avoid undue reaction with and loss of catalytic promoting materials. Thus it is advantageous that the support be calcined, e.g. at temperatures of about 600° to 1500° F. or more, to reduce the water content, but such calcination should not be so severe that the support is no longer catalytically-active.

The support component can contain other materials in addition to silica which materials, when combined with silica, provide an acidic material as in, for instance, the case of silica-alumina. Often these materials are one or more oxides of the metals of Groups II, III and IV of the Periodic Table. Examples of the composites contemplated herein under the generic designation of silica-based materials are often composed predominantly of or even to a major extent of silica. These supports include, for example, silica-alumina, silica-boria, silica-zirconia, silica-magnesia, silica-alumina-zirconia, silica-alumina-thoria, silica-alumina-magnesia, and the like. The silica-based support can contain amorphous or crystalline materials such as a crystalline aluminosilicate, for instance, having pore openings with diameters in the 6 to 15 Angstrom unit range. The support often contains silica and alumina, and such supports, whether naturally-occurring as in acid-treated clays, or a synthetic gel, will frequently contain about 10 to 60, preferably about 15 to 45, weight percent alumina. In addition, such silica-alumina supports can, and preferably do, contain a portion of the alumina as a separate, distinct phase.

A highly preferred catalyst support can be made by combining a silica-alumina hydrogel with a hydrous alumina with or without (preferably without) a crystalline aluminosilicate. An advantageous hydrous alumina component is, when analyzed by X-ray diffraction of dry samples, either one or a mixture of amorphous hydrous alumina and a monohydrate, e.g., boehmite, of less than about 50 Å, preferably less than about 40 Å, crystallite size as determined by half-width measurements of the (0,4,1) X-ray diffraction line calculated by the Debye-Scherrer equation. The mixture of the catalyst precursor components can be dried, e.g., at about 220° to 500° F., to provide the active catalyst support. During calcination, the separate hydrous alumina phase of the mixture is converted to a gamma form or other catalytically-active alumina.

In providing the preferred catalyst support precursor for drying, the components can be combined in any suitable manner or order desired, and advantageously each of the components in the mixture is in finely-divided form, preferably the particles are principally less than about 300 mesh in size. The finely-divided material can have an average particle size of about 10 to 150 microns and can be used to make a catalyst of this particle size which can be employed in a fluidized bed type of operation. However, if desired, the mixture of catalyst support components can be placed in macrosized form, that is, made into particles as by tabletting, extruding, etc., to sizes of the order of about 1/64" to ½" or more in diameter and about 1/32" to 1" or more in length, before or after drying or calcination. If formation of the macrosized particles is subsequent to calcination and the calcined particles have been contacted with water, the material can be recalcined.

On a dry basis, the preferred supports of the catalysts of the present invention contain about 45 to 95 weight percent of the amorphous silica-alumina xerogel, about 5 to 55 weight percent of the separately added alumina phase, and about 0 to 50 weight percent of the crystalline aluminosilicate, preferably the proportions of these ingredients are about 75 to 90%, about 10 to 25% and about 0 to 20%, respectively. If present, the crystalline aluminosilicate is usually at least about 1 weight percent, preferably at least about 5 weight percent, based on the dried support.

The alumina content from the silica-alumina xerogel and the separate alumina phase is about 20 to 70 weight percent, preferably about 25 to 60 weight percent, based on the dried support. Also, the catalyst support generally contains less than about 1.5 weight percent, preferably less than about 0.5 weight percent, sodium.

The silica-alumina component of the precursor of the preferred catalyst support of the present invention can be silica-alumina hydrogel which contains about 55 to 90, preferably 65 to 75, weight percent silica and about 10 to 45, preferably about 25 to 35, weight percent alumina, on a dry basis. The silica-alumina can be naturally-occurring or can be synthetically prepared by any desired method and several procedures are known in the art. For instance, an amorphous silica-alumina hydrogel can be prepared by co-precipitation or sequential precipitation by either component being the initial material with at least the principal part of the silica or alumina being made in the presence of the other. Generally the alumina is precipitated in the presence of a silica gel. It is preferred that the silica-alumina hydrogel be made by forming a silica hydrogel by precipitation from an alkali metal silicate solution and an acid such as sulfuric acid. Then alum solution may be added to the silica hydrogel slurry. The alumina is then precipitated by raising the pH into the alkaline range by the addition of an aqueous sodium aluminate solution or by the addition of a base such as ammonium hydroxide. Other techniques for preparing the silica-alumina hydrogel are well known in the art, and these techniques may be used in the practice of the invention.

The alumina hydrogel which can be combined with the silica-alumina is made separately from the silica-alumina.

The alumina hydrogel may be prepared, for example, by precipitation of alumina at alkaline pH by mixing alum with sodium aluminate in an aqueous solution or with a base such as soda ash, ammonia, etc. As noted above the alumina hydrogel can be in the form of amorphous hydrous alumina or alumina monohydrate, e.g., of up to about 50 Å crystallite size as determined by X-ray diffraction analysis. The amorphous hydrous alumina generally contains as much combined water as does an alumina monohydrate. Mixtures of the monohydrate and amorphous forms of hydrous alumina are preferred and often this phase is composed of at least about 25% of each of the separate members.

In preparing the catalyst support, we may separately filter the silica-alumina hydrogel and the hydrous alumina and intimately mix these materials, for instance, by colloidal milling. Although in this particular procedure a low sodium content crystalline aluminosilicate can be added after the milling, this ingredient can also be combined before the colloidal milling operation. The mixture is dried, water washed to acceptable concentrations of, for instance, sodium, and redried in the preferred procedure. The drying, especially the initial drying, is advantageously effected by spray drying to give microspheres.

The crystalline aluminosilicate which can be present in catalyst support of the present invention, can have pore openings of about 6 to 15 Å in diameter and preferably the pore openings have a diameter of about 8 or 10 to 14 Å. Usually, with a given material, the pores are relatively uniform in size and often the crystalline aluminosilicate particles are primarily less than about 15 microns in size, preferably less than about 10 microns. In the crystalline aluminosilicate, the silica-to-alumina mole ratio is often greater than about 2:1 and is usually not above about 12:1, preferably being about 4 to 6:1. The aluminosilicate may be available in the sodium form, and sodium can be removed before or after the crystalline aluminosilicate is added to the other catalyst support ingredients.

It is preferred to exchange the sodium with ammonium ions, for instance, through contact with an aqueous solution of ammonium chloride or another water-soluble ammonium compound. Subsequently, during drying and/or calcination, the ammonium ion may break down to release ammonia and leave an acid site on the aluminosilicate. On a molar basis, the ammonium or hydrogen ion is usually at least about 10% or even at least about 50%, based on the alumina content of the crystalline aluminosilicate. Suitable replacements for the sodium also include the polyvalent metals of the periodic chart, including the Group II-A and rare earth metals such as cerium, etc. The metals may be present along with the ammonium or hydrogen cations.

The order in which components are combined to prepare the supported catalyst of the present invention can be varied. The catalysts can be conveniently prepared by impregnating the silica-based support material with a solution of the palladium component, e.g., palladium acetylacetonate, in a solvent, e.g., methanol. The palladium-impregnated support, preferably after solvent removal, may then be sequentially contacted with a solution of the monotertiary phosphine electron donor ligand component, e.g., triphenyl phosphine, and then the reducing agent and Lewis acid component or components, e.g. ethyl aluminum sesquichloride or diethyl aluminum chloride. The catalysts prepared according to this method wherein the $\pi$-allyl palladium complex is formed on the support material generally exhibit less activity than the types described hereinafter wherein the $\pi$-allyl complex is prepared in the presence of a conjugated diene of the type used in making the diene-monene dimers in accordance with this invention, e.g., 1,3-butadiene. The presence of the conjugated diene during catalyst preparation is believed to aid formation of an at least initially more active catalyst species.

Thus, although the foregoing are methods for preparing the catalysts of this invention, in a first more preferred method the palladium source is supported on the acidic, solid, silica-based material in the presence of a monotertiary phosphine electron donor ligand, e.g., triphenyl phosphine, and subsequently reduced to the active catalyst with the Lewis acid-reducing agent components or component, e.g., diethylaluminum chloride, in the presence of a conjugated diene, e.g., 1,3-butadiene. In a second more preferred method, a π-allyl palladium complex is prepared from a palladium source, e.g., palladium acetylacetonate, a monotertiary phosphine electron donor ligand, e.g., triphenyl phosphine, and the Lewis acid-reducing agent component or components, e.g., diethylaluminum chloride, in an inert solvent in the presence of a conjugated diene, e.g., 1,3-butadiene, before the acidic, solid, silica-based material is added to the system to fix the palladium source and form an active, stable catalytic species. The catalysts prepared by the first preferred method will hereinafter be referred to as catalyst type A while those of the second preferred method will hereinafter be referred to as catalyst type B. The foregoing are two general methods for preparing the preferred catalysts of this invention, types A and B. Type B has generally been found to be the more advantageous regarding activity and stability of these two types.

More specifically, in the preparation of the B type catalysts, the π-allyl palladium complex is first prepared for subsequent impregnation into the silica-based support. The preparation of the π-allyl-palladium complex is normally conducted by mixing a palladium source, an electron donor ligand and a Lewis acid-reducing component in an inert solvent and bubbling a conjugated diene through the system before addition of the support. Suitable solvents are those which are inert to the catalyst and which will not enter into or deleteriously affect the eventual codimerization reaction. As specific examples thereof may be mentioned aromatic and aliphatic hydrocarbons such as hexane, benzene, toluene, and various petroleum fractions. Oxygen- and halogen-containing solvents are generally to be avoided during the codimerization. Suitable solvents for the complex-forming reaction thus generally are the same solvents which are suitable for use with the final catalyst composition in a reactive environment. If desired, however, the complexing may be accomplished in a solvent which is unsuitable for use with the final composition; in this case, the resultant complex can be first isolated from the reaction mixture and re-dissolved or re-suspended in a proper solvent which is inert to the final catalyst composition.

The codimerization of conjugated dienes with monoenes to form trans-1,4 dienes using the catalysts herein can be accomplished using short reaction times and mild reaction conditions. Various conjugated dienes are useful in the disclosed process, although those 1,3-dienes having up to about 10 carbon atoms such as butadiene, isoprene, piperylene, 1,3-cyclopentadiene and 1,3-cyclooctadiene, including their halogen, alkyl and phenyl-substituted derivatives such as chloroprene and 2-phenyl butadiene are preferred. Various monoenes are useful, although olefins of up to about 10 carbon atoms such as ethylene, propylene, isobutylene, pentene-1 and other α-olefins are preferred. The reaction may generally be conducted over a wide range of temperatures and pressures. Normally, the reaction is conducted in the liquid or gaseous phase at a temperature above room temperature in the range of from about 75° F. to about 300° F. The reaction is also normally carried out using pressures greater than atmospheric wherein the additional pressure is at least partially supplied by the monoene reactant. Thus, the reaction is conducted up to about 5000 p.s.i.g., preferably from about 500 p.s.i.g. to 2000 p.s.i.g. The optimum combinations of temperature, pressure, reaction time, reactants and catalyst may be determined from variation of the reaction parameters. The reaction may furthermore be optionally accomplished in the presence of an inert, organic solvent. Useful solvents are hydrocarbons such as hexane, toluene, benzene, and petroleum fractions boiling between about 150° to 350° F. Also, the amount of catalyst present during the reaction can vary, but the amount is often from about 0.01 to 20% by weight of the reactants. In continuous reaction systems the space velocity may normally be about 1 to 25 WHSV, preferably about 2 to 15 WHSV.

The following Examples I to III relate to the preparation of a preferred type of solid, silica-based support material, which material has an additional alumina phase.

EXAMPLE I

An alumina hydrogel is prepared as follows:

In a tank containing 5700 gallons of water at 85° F., are dissolved 300 lbs. of soda ash. When the soda ash has been dissolved, 180 gallons of a 39% concentration aqueous sodium aluminate solution are pumped into the tank in about a 15-minute period. The contents of the tank are at about 84° F. and six-hundred gallons of aqueous aluminum sulfate of 7.8% concentration, as $Al_2O_3$, are added to the admixture over an 80-minute period with water of dilution in conjunction with, and in addition thereto, diluting the reaction mass at a rate of 25 gallons per minute.

The pH of the resulting aqueous reaction mass is adjusted to 8.0 with about 75 gallons of 39% concentration aqueous sodium aluminate solution which, while being added, is also diluted continuously with water at a rate of 35 gallosn per minute over a 7½ minute addition period. The contents of the tank are heated to about 100° F., and pumped to storage.

The precipitated, hydrated alumina is thereafter filtered on a large gel filter. The filtered product is partially purified by a one-cycle, water-wash on the filter on which it is collected. This filter is a string vacuum type drum filter with a built-in water spray nozzle directed toward the filter drum. Material on the drum is contacted with water as the drum rotates past the nozzle. After washing, the wet alumina hydrogel is stripped from the drum. This hydrogel analyzes about 50% boehmite having a crystallite size of about 35 Å, and 50% amorphous hydrous alumina as determined by X-ray diffraction on dried samples.

EXAMPLE II

A silica-alumina hydrogel is prepared by the following technique:

To a batch tank is added 4,275 gallons of water preheated to 90° F., and 865 gallons of sodium silicate solution (28.8 weight percent $SiO_2$, 40–41.5 Baume at 68° F. and $Na_2O:SiO_2$ ratio of 1:3.2) is added. The batch is stirred for five minutes. The concentration of the sodium silicate, as $SiO_2$, in the batch is 6.3 weight percent.

With the batch at 90° F., 302 gallons of 34.5 weight percent sulfuric acid solution at 182° F. are added over a period of 45 minutes. The gel forms about 35 minutes after acid addition is begun. Then the pH is adjusted to 8.0–8.5. The batch is agitated for ten minutes.

Then 715 gallons of alum (7.8 weight percent, as $Al_2)_3$) is added to the gel over a period of about 36 minutes. The batch is agitated for an additional five minutes whereupon 205 gallons of sodium aluminate solution (24.4 weight percent as $Al_2O_3$) diluted in 1080 gallons of water is added over a period of 17 minutes. After all the sodium aluminate is added, the pH is checked. It should be between 5.0 and 5.2. The alumina content of the silica-alumina hydrogel is 30–31%.

EXAMPLE III

The silica-alumina hydrogel product of Example II and 1740 gallons of the alumina hydrogel filter cake of Example I are mixed together for one hour. The finished batch has a pH of 5.5 to 5.6 and a temperature of about 110° F. The aqueous gel mixture is then pumped to a dewatering filter, and the filter cake from said dewatering filter and a portion of aqueous gel are blended to give a gel slurry of about 14 weight percent solids. A portion of this hydrogel mixture was slurried, as a thick flowable paste, with a "Lightnin" stirrer fitted with a cage-beater and a propellor, for about 10 minutes to give a thorough dispersion. The product was stirred one minute at 14,500 r.p.m., in a Waring Blender and dried in a laboratory spray-drier. The spray-dried material was washed with water to acceptable impurity levels and dried at 230° F. The washed and dried material analyzed 0.08% $SO_4$ and less than 25 p.p.m. $Na_2O$. The dried material as such was used as the catalyst support, as were extruded forms thereof and tablets (pellets) having diameters of about ⅛ inch and lengths of about ⅛ to ¼ inch. Before use the catalyst support was calcined in a muffle furnace by raising the temperature by 300° F. per hour until 1350° F. was reached. This temperature was then held for three hours. The calcined particles had a surface area of about 320 to 340 square meters per gram.

The remainder of the Examples are drawn to the preparation of the π-allyl complex catalyst compositons and the use thereof in the codimerization of conjugated dienes and monoenes, particularly 1,3-butadiene and ethylene, to form trans-1,4-dienes, particularly trans-1,4-hexadiene. The following examples are further indicative of the stability of the solid catalysts prepared herein. Tables I and II give further details of catalyst compositions, reaction conditions and product distribution.

EXAMPLE IV

The preparation of a type A catalyst is accomplished as follows:

0.32 Grams of palladium acetylacetonate, 1.41 grams of triphenylphosphine and 5.0 grams of the extrudate silica-alumina support of Example III are mixed in 35 ml. of toluene at room temperature and allowed to stand under a nitrogen atmosphere for about twenty hours. The support extrudate is then washed with about 100 ml. of toluene until a colorless supernatant liquid is obtained. All remaining toluene is decanted and the pellets are transferred with 25 ml. of fresh toluene to a 300 cc. stainless steel magnedrive autoclave, which is sealed and flushed with purified nitrogen. Then 25 ml. of toluene and 5 ml. of diethylaluminum chloride (a 36.1% solution thereof in toluene) are transferred to a 75 cc. nitrogen blanketed stainless steel bomb which is then sealed and pressured with 400 p.s.i.g. of nitrogen.

Ten ml. of butadiene is added to the autoclave and the pressurized addition of the contents of the steel bomb to the autoclave is accomplished. The addition of butadiene may also follow the addition of the diethylaluminum chloride.

EXAMPLE V

The preparation of a type B catalyst is accomplished as follows:

10.4 Grams of a 36.1% diethylaluminum chloride solution in toluene is added to 0.32 grams of palladium acetylacetonate, 1.32 grams of triphenylphosphine and 20 ml. of butadiene in a benzene solution in a nitrogen blanketed dry box at room temperature. Then the butadiene is evaporated off and 5.0 grams of the extrudate silica-alumina support of Example III is added to the homogeneous yellow solution. After remaining open to the atmosphere for about 48 hours, the dry box is emptied; then the solvent is removed and the extrudate pellets are transferred to a 300 cc. autoclave which is sealed and flushed with purified nitrogen.

EXAMPLE VI

As in Example IV, butadiene (10 ml.) is added to the sealed autoclave followed by the pressurized addition of the entire contents of the 75 cc. stainless steel bomb as described in Example IV. Additional butadiene (35 ml.) is subsequently added to the autoclave followed by 300 psig of ethylene. The heater is turned on accompanied by the stirrer and the reaction begun. A heat-up time of one hour is required to bring the temperature of the system to 180° F. This temperature (±10° F.) is maintained throughout the 21.0 hour reaction time. A pressure range of 850–1050 psig is recorded for the 21 hour reaction time. A clear yellow liquid product (88 gms.) is collected using a dry ice-acetone trap, transferred to a 150 cc. stainless steel bomb, and analyzed by gas chromatography. The calculated butadiene conversion for this reaction is about 97% with a selectivity to trans-1,4-hexadiene of 5.3%. Considerable isomerization took place as observed by the conjugate 2,4-hexadiene (cis and trans isomers) content (45.1%). Pertinent data regarding this run are listed in Tables I and II.

EXAMPLE VII

In the manner described in Example IV palladium acetylacetonate (0.31 gms.) and triphenylphosphine (1.34 gms.) are supported on the silica-alumina extrudate (5.1 gms.) of Example III. The supported pellets are transferred to the 300 cc. magnedrive autoclave along with fresh toluene (50 ml.), mixed with butadiene (20 ml.), and activated with diethylaluminum chloride (5 ml. of a 36.1% toluene solution) in 25 ml. of additional toluene. Ethylene (650 psig) is subsequently added and the heater turned on accompanied by the stirrer. A heat-up time of about 1.5 hours is required to reach the desired temperature of 150° F. which is maintained for the 19.5 hour reaction period. A pressure of 1200±50 psig is also maintained for this period of time. A yellow-tinted product (82 gms.) collected using a dry-ice-acetone trap is slowly warmed to room temperature, providing a sample (78.6 gms.) for gas chromatography analysis. The butadiene conversion is approximately 70% and the selectivity to trans-1,4-hexadiene is about 4.0%. The extent of isomerization, although less than Example VI, is substantial as witnessed by the 2,4-hexadiene content (37.5%). As before, all data are listed in Tables I and II which more completely describe this run.

EXAMPLE VIII

As described in Examples IV and VII the heterogeneous catalyst is prepared from palladium acetylacetonate (0.33 gms.) and triphenylphosphine (1.39 gms.) using the extrudate (5.0 gms.) of Example III in a toluene solvent (50 m.). The supporting pellets are then activated in butadiene (25 ml.) with diethylaluminum chloride (5 ml. of a 36.1% toluene solution) in 15 ml. of additional toluene in a fashion as previously outlined. Additional butadiene (15 ml.) is added to the autoclave containing the above components followed by ethylene (300 psig). The heater is turned on accompanied by the stirrer; a 45 min. heat-up period is required to attain the desired temperature of 173° F. which is held throughout the 10.5 hour reaction period. The pressure is maintained at 1100±50 psig throughout. After 10.5 hours reaction time, the product (155.5 gms) is transferred directly to a 300 cc. stainless steel bomb at dry ice-acetone temperature. The catalyst is retained in the sealed autoclave and the stainless steel bomb at −80° C. was slowly vented off (∼24 hours) leaving a product (89.5 gms.) which is analyzed by gas chromatography. The conversion calculates to be 82.3% based on butadiene charged, and the selectivity to trans-1,4-hexadiene is 11.0%. The extent of isomerization is about the same as Example VI. Tables I and II contain the data accumulated for this run.

EXAMPLE IX

Using the catalyst left in the 300 cc. autoclave from Example VIII, a second consecutive reaction is begun with butadiene (40 ml.) and ethylene (1100 psig). A 45-min. heat-up time is required to reach the same temperature (173° F.) as used in Example VIII. This reaction (10.5 hours) is also carried out at 173° F. and 1100 psig. After the stated reaction time, the product (67.0 gms.) is treated as explained in Example VIII to provide the final gas chromatographic sample product (26.5 gms.) for analysis. The catalyst is again retained in the autoclave for further use.

The conversion recorded for this reaction is 20.8% and the selectivity to trans-1,-,4-hexadiene is 52.1%. As reported in Table I the conversion is reduced from that obtained in example VIII while the selectivity is increased from Example VIII. Additional comparative data is listed in Table II.

EXAMPLE X

Using the catalyst left in the 300 cc. autoclave from Example IX, a third consecutive reaction is begun with butadiene (40 ml.) and ethylene (1100 psig). Except for a reaction time of 7.5 hours, all conditions of the reaction and work-up procedures are the same. A final product (25.5 gms.) is analyzed by gas chromatography. The conversion (50.0%) is increased over Example IX while the selectivity (51.2%) remains unchanged.

EXAMPLE XI

Butadiene (50 ml.) and ethylene (∼800 psig) are introduced to the 500 cc. autoclave containing the catalyst of Example V. The heater and stirrer are turned on and an about 10 hour reaction begun. A temperature of 170°±10° F. and a pressure of 1300±100 psig is maintained. A yellow colored product (65 gms.) is collected and transferred to a sampling bomb resulting in a product (59.8 gms.) which is analyzed by gas chromatography. The catalyst from this reaction is removed from the autoclave and stored in air for two hours after use. The conversion calculated for this reaction is 43.8% and the selectivity to the trans-1, 4-hexadiene is 65.5%. The extent of isomerization is comparatively low (13.1%) as reflected by the conjugated $C_6=$=content. Tables I and II contain additional pertinent data.

EXAMPLE XII

After being stored for 2 hours in an air atmosphere the catalyst employed in Example XI is transferred back to the 300 cc. autoclave along with additional triphenylphosphine (1.32 gms.), butadiene (40 ml.), and toluene (50 ml.). Diethylaluminum chloride (5 ml. of a 36.1% toluene solution) is added followed by ethylene (∼650 psig), and the heater and stirer are turned on for a second consecutive reaction. The conditions for this reaction are comparable to Example XI and are listed in Table I. Both the conversion (30.0%) and selectivity (51.6%) for this reaction decrease from the first run (Example XI). Additional comparisons may be found in Tables I and II.

EXAMPLE XIII

To a 250 ml. four-neck flask are added palladium acetylacetonate (0.33 gms.), triphenylphosphine (1.36 gms.) and chloroform (70 ml.) and the system is flushed with prepurified nitrogen. Butadiene (∼25 ml.) is subsequently added until a steady reflux is obtained from the dry ice-acetone cold finger. Diethylaluminum chloride (10 ml. of a 36.1% toluene solution) is added to give a homogeneous-yellow solution. Approximately two hours later the extrudate of Example III (5.0 gms.) is added, and the system is maintained overnight with a slow nitrogen bleed (∼20 hours). The liquid is decanted from the pellets and the pellets rinsed with about 50 ml. of chloroform until a colorless supernatant liquid is obtained. The residual chloroform is removed from the pellets under a vacuum of about 10 mm. for about 5 min. and the dried pellets are introduced into the autoclave. The autoclave is sealed and flushed well with nitrogen. Butadiene (100 ml.) is added to the reactor followed by ethylene (500 psig). The heater and stirrer are turned on and approximately one hour is required to heat the system to the desired temperature (176° F.). At this temperature a pressure of 1200±100 psig is maintained throughout the four hour reaction period. The product from this reaction is pressurized into a 300 cc. stainless steel bomb and the ethylene is then slowly bled off leaving a product mixture (84.5 gms.) which is analyzed by gas chromatography. The conversion is 55.8% with a selectivity of 44.4% to the trans-1,4-hexadiene. Isomerization to the conjugated diolefin is still substantial as shown by the 2,4-hexadiene content (31.0%). All other recorded data from this experiment may be found in Tables I and II.

EXAMPLE XIV

Using the same procedure as outlined in Example XIII, the catalyst is prepared from palladium acetylacetonate (0.32 gms.), triphenylphosphine (1.38 gms.), butadiene (∼25 ml.), and diethylaluminum chloride (10 ml. of a 36.1% toluene solution) in toluene (50 ml.) solvent. 5.0 Grams of the extrudate of Example III is added to the above system and retained for about 20 hours. After freeing the solvent from the pellets, they are transferred to the autoclave which is then sealed and flushed with nitrogen. Butadiene (140 ml.) is added along with ethylene (400 psig). The heater and stirrer are turned on and a heat-up time of one hour is required to reach the desired temperature (175° F.) for the six hour reaction. A continuous ethylene pressure (1200 psig) is maintained throughout the reaction period. A sample of the reactor liquid phase is taken immediately after the above-mentioned heat-up time. Additional samples are similarly taken every 1.5 hours for the complete reaction period. These samples are then analyzed by gas chromatography. Results from these samplings are recorded in Tables I and II.

EXAMPLE XV

Palladium acetylacetonate (0.32 gms.), triphenylphosphine (1.34 gms.), and toluene (5 ml.) are placed in an autoclave which is sealed and flushed with nitrogen. Butadiene (100 ml.) is then added. A mixture of toluene (10 ml.) and diethylaluminum chloride (10 ml. of a 36.1% toluene solution) is then added followed by ethylene (500 psig). The heater and stirrer are turned on and a pressure of 1200±100 psig is maintained along with a temperature of 175° F. for a four hour reaction period. The product is collected in a 300 cc. stainless steel bomb containing dilute HCl (25 gms.). The ethylene is vented off, and the separated product phase (48 gms.) is analyzed by gas chromatography. The conversion based on butadiene charged is calculated to be 17.5% and the selectivity to trans-1,4-hexadiene 37.5%. The extent of isomerization is substantial as indicated by the content of 2,4-hexadiene (35.0%). Tables I and II contain information recorded for this experiment.

EXAMPLE XVI

To examine the extent of the isomerization of 1,4-diene products by the $\pi$-allyl palladium complex supported on the extrudate of Example III, the same run described in Example XIV is duplicated over a 3.75 hour period by taking four samples from the system as reaction progressed. Palladium acetylacetonate (0.35 g.), 1.32 g. triphenylphosphine, and 50 ml. chloroform are placed in a 250 ml. flask giving a yellow homogeneous solution. Butadiene is then added until a steady reflux is obtained off a dry ice-acetone cold finger under a nitrogen atmosphere. Diethylaluminum chloride (20 ml. of a 36.1% toluene solution) is introduced to the refluxing system giving a homogeneous light yellow solution. After the system is allowed to react under the refluxing conditions for a two hour period, the yellow $\pi$-allyl complex solution of palladium is poured on to 5.0 grams of extrudate of Example III in a Erlenmeyer flask. The contents of the flask are stirred overnight allowing the excess amount of unreacted butadiene to evaporate off. The resulting tan colored catalyst extrudates are filtered and washed with about 100 ml. of chloroform until a colorless supernatant liquid is obtained. These steps are carried out under a nitrogen atmosphere. The resulting tan colored catalyst pellets are drained of solvent and put under vacuum to remove as much solvent as possible. The catalyst pellets are charged in a 300 cc. autoclave equipped with a magnetic stirrer, and both butadiene (140 ml.) and ethylene (400 psig at room temperature) are fed to the autoclave. The heater and stirrer are turned on and within 40 minutes the reactor reaches a temperature of 161° F. and a pressure of 1140 psig. Four samples (~1 ml.) are taken out of the reactor during the time span of 3 hours to study the extent of isomerization of the trans-1,4-diene product and of the conversion of the butadiene feed. These samples are subjected to the gas chromatographic analyses. The results are listed in Tables I–II. The data clearly indicates that the isomerization of 1,4-dienes to 2,4-isomer takes place rapidly as the contact time of the reaction mixture to the catalyst lengthens, and that the conversion of the butadiene feed (91 g.) increases from 8% to 26% during a 3 hour reaction period.

EXAMPLE XVII

The catalyst used in the reaction of Example XVI is aged under an ethylene atmosphere for 35 days. The reaction of Example XVI is then substantially duplicated. The results of the reaction with this aged catalyst are summarized in Tables I and II and indicate clearly that the aged catalyst is still an active catalyst.

A study of the data presented in Tables I and II indicates that catalyst Type A gives a less selective reaction to the desired 1,4-hexadiene products and less isomerization of the trans-1,4-diene to conjugated diene products, particularly 2,4-dienes, than does catalyst type B. Again, it is believed this reduced activity is due to the absence of conjugated diene during catalyst formation. Thus, using Catalyst A a diene is present only when the codimerization is initiated. Furthermore, the extent of isomerization of trans-1,4-hexadiene to 2,4-hexadienes increases with the length of reaction as indicated by Examples XIV and XVI. Also, the 2,4-dienes then appear to react with another ethylene molecule to give a 1,4-diene; in this particular case the 1,4-diene is 3-methyl-1,4-heptadiene. Examples XI and XII indicate that the solid catalysts used herein are extremely stable upon exposure to the atmosphere.

TABLE I

| Example No. | Catalyst Composition | | | | Solvent g. $\phi CH_3$ | Reaction Conditions | | |
|---|---|---|---|---|---|---|---|---|
| | Pd(acac)$_2$ g. | $\phi_3$P g. | Et$_2$AlCl g. | Alumina-Silica Support g. | | Time Hr. | Temperature °F. | Pressure Psig. |
| VI | 0.32A | 1.41 | 1.62 | 5.0 | 43.0 | 21.0 | 170–192 | 850–1050 |
| VII | 0.31A | 1.34 | 1.62 | 5.1 | 64.5 | 19.5 | 150 | 1200 |
| VIII | 0.33A | 1.39 | 1.62 | 5.0 | 43.0 | 10.5 | 173 | 1100 |
| IX | 0.33A | 1.39 | 1.62 | 5.0 | 43.0 | 10.5 | 173 | 1100 |
| X | 0.33A | 1.39 | 1.62 | 5.0 | 43.0 | 7.5 | 173 | 1100 |
| XI | 0.32B | 1.32 | 3.75 | 5.0 | 43.5 | 19 | 160–182 | 1300 |
| XII | 0.32B | 1.32 | 1.62 | 5.0 | 86.0 | 18 | 170–185 | 1500–1700 |
| XIII | 0.33B | 1.36 | 3.2 | 5.0 | — | 4.0 | 176 | 1200 |
| XIV 1. | 0.32B | 1.38 | 3.2 | 5.0 | — | 0.0 | 175 | 1200 |
| 2. | <0.32B | <1.38 | <3.2 | 5.0 | — | 3.0 | 175 | 1200 |
| 3. | <0.32B | <1.38 | <3.2 | 5.0 | — | 4.5 | 175 | 1200 |
| 4. | <0.32B | <1.38 | <3.2 | 5.0 | — | 6.0 | 175 | 1200 |
| XV | 0.32B | 1.34 | 3.2 | — | 12.0 | 4.0 | 175 | 1200–1300 |
| XVI 1. | 0.35B | 1.32 | 6.4 | 5.0 | — | 0.75 | 160 | 1100 |

TABLE I-continued

| | Catalyst Composition | | | | Solvent | Reaction Conditions | | |
|---|---|---|---|---|---|---|---|---|
| Example No. | Pd(acac)₂ g. | φ₃P g. | Et₂AlCl g. | Alumina-Silica Support g. | g. φCH₃ | Time Hr. | Temperature °F. | Pressure Psig. |
| 2. | <0.35B | <1.32 | <6.4 | 5.0 | — | 1.75 | 160 | 1100 |
| 10   3. | <0.35B | <1.32 | <6.4 | 5.0 | — | 2.75 | 160 | 1100 |
| 4. | <0.35B | <1.32 | <6.4 | 5.0 | — | 3.75 | 160 | 1100 |
| XVII | <0.35 | <1.32 | <6.4 | 5.0 | — | 7.5 | ~165 | 1050–1350 |

A:Cat A
B:Cat B

TABLE II

| | Feed | | Conversion to | Conversion to | Product Distribution | | | | | | | | 1,4-Hexadiene Product Ratio | |
|---|---|---|---|---|---|---|---|---|---|---|---|---|---|---|
| | | | | | Hexadienes | | | | | 3-Methyl hepta-diene | 4-Vinyl cyclo-hexane | Unknown | | |
| Ex. No. | 1,3-BD/C₂= g. | psig | B-D, % | t-c₆==, % | t-1,4 | c-1,4 | t+c 1,5 | t+c 1,3 | t+c 2,4 | | | | t-1,4/ c-1,4 | t-1,4 c-2,4 |
| VI | 29.3 | 300 | 97 | 5.3 | 5.3 | 1.2 | 0.3 | — | 45.1 | — | 28.4 | 19.7 | 4.4 | 0.1 |
| VII | 13.0 | 650 | 70 | 4.0 | 4.0 | 0.7 | 0.2 | — | 37.5 | — | 0.3 | 57.3 | 5.5 | 0.1 |
| VIII | 26.0 | 300 | 82.3 | 11.0 | 11.0 | 2.9 | 0.4 | 0.9 | 45.2 | 10.6 | 0.7 | 28.3 | 3.8 | 0.3 |
| IX | 26.0 | 300 | 20.8 | 52.1 | 52.1 | 11.0 | 0.3 | 0.5 | 11.4 | 1.9 | 12.9 | 9.8 | 4.7 | 5.5 |
| X | 26.0 | 300 | 50.0 | 51.2 | 51.2 | 12.8 | 0.4 | 0.6 | 11.5 | 0.5 | 13.3 | 9.7 | 4.0 | 5.6 |
| XI | 32.5 | 800 | 43.8 | 65.5 | 65.5 | 10.5 | — | — | 13.1 | — | 3.2 | 7.0 | 6.2 | 5.8 |
| XII | 26.0 | 650 | 30.0 | 51.6 | 51.6 | 8.7 | — | — | 9.6 | — | 16.4 | 13.7 | 5.9 | 6.3 |
| XIII | 65.0 | 500 | 55.8 | 44.4 | 44.4 | 7.9 | 0.8 | 1.2 | 31.0 | 1.8 | 2.5 | 10.4 | 5.6 | 1.7 |
| XIV-1 | 91.0 | 400 | 7.6 | 43.8 | 43.8 | 6.3 | — | 4.2 | 6.3 | — | 33.3 | 10.4 | 7.0 | 8.0 |
| 2 | 91.0 | 400 | 68.2 | 43.9 | 43.9 | 7.4 | 0.7 | 1.2 | 32.4 | 1.6 | 2.3 | 11.5 | 5.9 | 1.6 |
| 3 | 91.0 | 400 | 81.2 | 38.2 | 38.2 | 6.7 | 0.7 | 1.2 | 37.3 | 2.6 | 1.8 | 8.7 | 5.7 | 1.2 |
| 4 | 91.0 | 400 | 90.0 | 36.7 | 36.7 | 6.2 | 0.8 | 1.1 | 41.7 | 3.4 | 1.5 | 10.4 | 5.9 | 1.0 |
| XV | 65.0 | 500 | 17.5 | 37.5 | 37.5 | 4.1 | 0.7 | 1.8 | 35.0 | 0.1 | 2.2 | 18.5 | 9.1 | 1.2 |
| XVI-1 | 91.0 | 400 | 8.2 | 49.6 | 49.6 | 10.9 | — | — | 2.2 | — | 34.3 | 2.9 | 4.5 | 27.7 |
| 2 | 91.0 | 400 | 16.8 | 52.9 | 52.9 | 11.1 | 0.3 | 0.7 | 14.1 | 0.7 | 15.7 | 4.2 | 4.8 | 4.5 |
| 3 | 91.0 | 400 | 20.7 | 58.9 | 58.9 | 12.4 | 0.4 | 0.4 | 9.5 | — | 13.9 | 5.4 | 4.8 | 7.5 |
| 4 | 91.0 | 400 | 26.0 | 60.2 | 60.2 | 13.1 | 0.4 | 0.6 | 10.6 | — | 10.2 | 4.9 | 4.6 | 6.0 |
| XVII | 81.0 | 400 | 18.0 | 43.8 | 43.8 | 6.7 | 0.2 | 0.5 | 12.3 | — | - - - - - 37.4 - - - - - | | 6.5 | 4.1 |

It is claimed:

1. A catalyst composition which comprises a minor amount of a π-allyl complex of:
   (A) a palladium source capable of forming a π-allyl complex,
   (B) a monotertiary phosphine electron donor ligand represented by the structural formula:

(R)₃P wherein R is hydrocarbyl having from 1 to about 20 carbon atoms,
   (C) combination of reducing agent capable of reducing the palladium to an oxidation state of less than 2 and Lewis acid capable of forming a coordination bond with palladium represented by the structural formula:

R'$_{(n-y)}$MX$_y$, wherein M is a metallic element of coordination number n whose halides are Lewis acids, X is a halogen having an atomic number of 9 to 53, R' is hydrocarbyl having up to about 20 carbon atoms, and y is a number having a value from 1 to at least one less than n, supported on
   (D) acidic, solid, silica-based material; wherein the molar ratio of (B) to (A) is from about 0.5 to 15:1, the molar ratio of (C) to (A) is from about 2 to 40:1 and the π-allyl complex is formed from a conjugated diene having up to 10 carbon atoms.

2. A composition of claim 1 wherein M is aluminum, X is chlorine and R' is alkyl having from 2 to about 10 carbon atoms.

3. A composition of claim 2 wherein the conjugated diene is 1,3-butadiene.

4. A composition of claim 1 wherein (A) is provided by a palladium chelate formed from a chelating compound selected from the group consisting of a β-diketone, a β-keto carboxylic acid, a β-keto carboxylic ester and a β-keto carboxylic salt.

5. A composition of claim 4 wherein (A) is provided by palladium acetylacetonate.

6. A composition of claim 1 wherein R is selected from the group consisting of alkyl having up to about 10 carbon atoms and phenyl.

7. A composition of claim 4 wherein (C) is an aluminum alkyl halide.

8. A composition of claim 1 wherein the weight ratio of (D) to (A) is from about 5 to 200:1.

9. A composition of claim 1 wherein the molar ratio of (B) to (A) is from about 3 to 10:1, the molar ratio of (C) to (A) is from about 5 to 12:1 and the weight ratio of (D) to (A) is from about 5 to 200:1.

10. A composition of claim 9 wherein R is selected from the group consisting of alkyl having up to about 10 carbon atoms and phenyl.

11. A composition of claim 10 wherein (C) is an alkyl aluminum halide.

* * * * *